United States Patent [19]

Hidaka et al.

[11] 4,230,455
[45] Oct. 28, 1980

[54] PROSTHETIC TEETH AND BONES

[75] Inventors: Tsuneo Hidaka; Masahide Inoue; Masatomi Ebihara, all of Tsurugashima, Japan

[73] Assignee: Asahi Kogaku Kogyo Kabushiki Kaisha, Tokyo, Japan

[21] Appl. No.: 966,233

[22] Filed: Dec. 4, 1978

Related U.S. Application Data

[63] Continuation-in-part of Ser. No. 804,476, Jun. 7, 1977, abandoned.

[30] Foreign Application Priority Data

Jun. 7, 1976 [JP] Japan .................................. 51-66217

[51] Int. Cl.$^3$ .............................................. A61C 13/08
[52] U.S. Cl. ................................... 433/202; 128/92 C
[58] Field of Search .......................... 32/10 A; 3/1.9; 106/73.1; 264/60, 16; 128/92 C; 433/202

[56] References Cited

U.S. PATENT DOCUMENTS

| | | | |
|---|---|---|---|
| 3,607,608 | 9/1971 | Siefert | 264/60 |
| 3,662,605 | 5/1972 | Boetz et al. | 3/1.9 |
| 3,787,900 | 1/1974 | McGee | 3/1.9 |

*Primary Examiner*—Robert Peshock
*Attorney, Agent, or Firm*—Sughrue, Rothwell, Mion, Zinn and Macpeak

[57] ABSTRACT

Prosthetic teeth and bones having superior affinity for the living body and having a compression strength of about $4 \times 10^{-3}$ kg/cm$^2$ or higher and a flexural strength of about $2.7 \times 10^3$ kg/cm$^2$ or higher, which comprise a composite material comprising (a) a sufficiently fine powder having an average particle size of about 2 μm or less comprising at least 50% by weight of $Ca_{10}(PO_4)_6(OH)_2$ and not more than about 50% by weight of at least one additive selected from the group consisting of $Ca_3(PO_4)_2$, $AlPO_4$, $Al_2O_3$, $AlF_3$, $SiO_2$, $Mg(PO_4)_2$, and the fluorides, chlorides and oxides of Li, Na, K, Mg and Ca, and (b) at least one fibrous material having the coefficient of thermal expansion nearly equal to or slightly lower than that of the hydroxy-apatite selected from the group consisting of fibers, fine filaments and metal whiskers, ceramics or glass, said fibrous material being present at least 50 μm inside the surface of the prosthetic teeth and bones, and said composite material being cold compression-molded and then sintered.

8 Claims, 3 Drawing Figures

PROSTHETIC TEETH AND BONES

CROSS-REFERENCE OF THE RELATED APPLICATION

This application is a continuation-in-part application of U.S. Pat. application Ser. No. 804,476 filed June 7, 1977 and is now abandoned and is entitled "Process for Producing Prosthetic Teeth and Bones from Hydroxyapatite".

BACKGROUND OF THE INVENTION

1. Field of the Invention

This invention relates to prosthetic teeth and bones having superior affinity for the living body and high mechanical strength.

2. Description of the Prior Art

In recent years, the superior affinity of hydroxy-apatite, $Ca_{10}(PO_4)_6(OH)_2$, for the living body has attracted considerable attention, and application of hydroxy-apatite are expected to be found in prosthetic teeth and bones. The material obtained by ordinary sintering or hot-pressing of hydroxy-apatite, when observed macroscopically, has a dynamic isotropy (i.e., the sintered material is an agglomerated body of fine crystal particles, and shows macroscopically isotropical properties since the crystal axis of each crystal particles is randomly oriented), and therefore, cannot be oriented as in the case of a fibrous structure which is characteristic of hard tissues of the human body as teeth or bones.

In order to improve the mechanical strength of the sintered material of hydroxy-apatite per se, it is known to blend fibrous materials and other materials with hydroxy-apatite to obtain a composite material. However, specific attention has not been paid to the structure of the composite material from the standpoint of the orientation of a fibrous structure for the purpose of utilization as prosthetic teeth and bones.

SUMMARY OF THE INVENTION

An object of this invention therefore is to provide prosthetic teeth and bones having superior affinity for the living body and high mechanical strength, which comprise a composite material comprising a fibrous material and hydroxy-apatite.

DETAILED DESCRIPTION OF THE INVENTION

The hydroxy-apatite employed in this invention does not have to be 100% pure hydroxy-apatite, but may include a material which comprises about 50 to 99.9% by weight of $Ca_{10}(PO_4)_6(OH)_2$ and about 0.1 to 50% by weight of at least one compound selected from the group consisting of $Ca_3(PO_4)_2$, $AlPO_4$, $Al_2O_3$, $AlF_3$, $SiO_2$, and the fluorides, chlorides and oxides of Li, Na, K, Ca and Mg.

The suitable examples of the fluorides, chlorides and oxides of Li, Na, K, Ca and Mg include LiF, NaF, KF, NaCl, KCl, $Li_2O$, etc.

The hydroxy-apatite used in this invention must be a sufficiently fine powder, preferably having an average particle size of about 2 $\mu m$ or less.

The fibrous material used in this invention is at least one member selected from the group consisting of fibers, fine filaments and metal whiskers, ceramics or glass. Suitable examples of fibrous materials include glass fibers and fibers or filaments of silicon carbide, alumina, etc.

The amount of the fibrous material used varies depending upon the end-use of the final product (e.g., a prosthetic tooth versus a prosthetic bone), but is generally from about 2 to 30% by weight based on the weight of the composite.

If the fibrous material to be combined with hydroxy-apatite is chosen such that its coefficient of thermal expansion is nearly equal to, or slightly lower, than that of the hydroxy-apatite, i.e., the ratio of the coefficient of thermal expansion of the fibrous material to that of the hydroxy-apatite is 1:1 to greater than 0.98:1, the resulting composite has an even further improved mechanical strength.

The fibrous material is preferably present at least about 50 $\mu m$ inside the surface of the prosthetic teeth and bones. In other words, the fibrous material is not exposed on the surface of the final products. This can provide the advantages such that the fibrous material is selected only on the basis of the mechanical strength and is not necessary to consider the affinity of the fibrous material for the living body. As a result, the selection of fibrous material expands.

Figure 1:
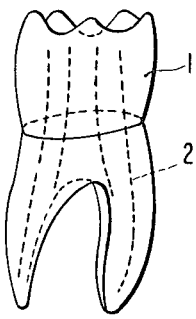
FIG. 1 is a schematic view of a prosthetic tooth according to the invention.
Figure 2:
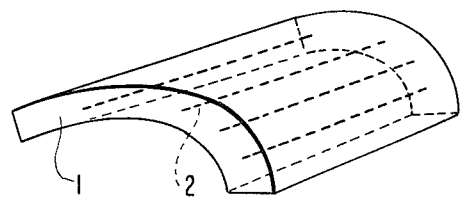
FIGS. 2 and 3 are schematic views of prosthetic bones according to the invention.
Figure 3:
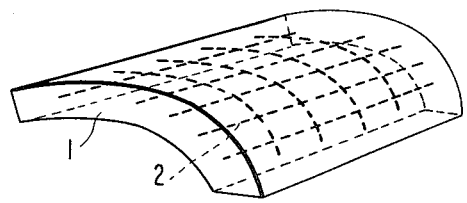

Some examples of the structure of a composite of the hydroxy-apatite powder and the fibrous material are shown in FIGS. 1, 2 and 3.

In the drawings, reference numeral 1 represents the powdery hydroxy-apatite, and 2, the fibrous material. FIG. 1 shows an example of a prosthetic tooth, and FIGS. 2 and 3 show examples of prosthetic bones. In FIGS. 1 and 2, the fibrous material is arranged in the same direction. In FIG. 3, the fibrous material is arranged both lengthwise and crosswise in the form of a fabric. Such a fabric can be e.g., woven or knitted.

The composite material of this invention is prepared by the following methods.

A fibrous material such as fibers, fine filaments, or metal whiskers, ceramics or glass are first placed in a mold having a shape corresponding to a tooth or bone to be formed and a sufficiently fine powder containing hydroxy-apatite, optionally together with a binder such as water or an aqueous solution of a resin such as polyvinyl alchol, is filled around the material so placed initially in the mold. The assembly is then cold compression-molded, e.g., at room temperature and under a pressure of about 50 to 1000 kg/cm$^2$ using metallic molds. This pre-forming (or cold-pressing) can also be performed using an isostatic press. The isostatic press includes a cold isostatic press (room temperature) and a hot isostatic press (e.g., an ultra high pressure of about 1 to 2 tons/cm$^2$ and a temperature a of about 1100° to 1350° C.), and the cold isostatic press and hot isostatic press can both be employed in this invention.

The pre-formed composite material is then sintered in a vacuum (e.g., $10^{-2}$ torr or less), in air, in an atmosphere of steam, or in an atmosphere of an inert gas, e.g., argon at a temperature of about 800° to about 1500° C. for about 15 minutes to about 40 hours.

As another method for preparing the composite material of this invention which is more important to prepare the composite materials shown in FIGS. 2 and 3, the fibrous material is interposed between two hydroxy-apatite layers which have previously been cold compression-molded, and then the assembly is cold compressed, followed by sintering under heat.

Since the composite material in accordance with this invention has a surface of hydroxy-apatite, it has superior affinity for the living body unlike those medical and dental materials comprising, for example, alumina, which are not in use. In addition, since the composite material has an internal fibrous structure, it has high compression strength, e.g., about $4 \times 10^3$ Kg/cm$^2$ or higher, and high flexural strength, e.g., about $2.7 \times 10^3$ kg/cm$^2$ or higher, and can function suitably as prosthetic teeth and bones. For example, a prosthesis for a bone having an improved flexural strength can be prepared by mixing hydroxy-apatite having an average particle size of 1.1 $\mu$m (95% by weight) with a woven silicate glass fiber fabric (5% by weight) containing silicate glass fibers of a diameter of 10 $\mu$m and subjecting such to the steps set forth above.

While the invention has been described in detail and with reference to specific embodiments thereof, it will be apparent to one skilled in the art that various changes and modifications can be made therein without departing from the spirit and scope thereof.

What is claimed is:

1. Prosthetic teeth and bones having superior affinity for the living body and having a compression strength of about $4 \times 10^3$ kg/cm$^2$ or higher and a flexural strength of about $2.7 \times 10^3$ kg/cm$^2$ or higher, which comprise a composite material comprising
   (a) a sufficiently fine powder having an average particle size of about 2 $\mu$m or less comprising at least 50% by weight of $Ca_{10}(PO_4)_6(OH)_2$ and not more than about 50% by weight of at least one additive selected from the group consisting of $Ca_3(PO_4)_2$, $AlPO_4$, $Al_2O_3$, $AlF_3$, $SiO_2$, $Mg(PO_4)_2$, and the fluorides, chlorides and oxides of Li, Na, K, Mg and Ca, and
   (b) at least one fibrous material having the coefficient of thermal expansion nearly equal to or slightly lower than that of the hydroxy-apatite selected from the group consisting of fibers, fine filaments and metal whiskers, ceramics or glass, said fibrous material being present at least 50 $\mu$m inside the surface of the prosthetic teeth and bones, and said composite material being a laminate of said fibrous material interposed between two layers of said fine powder and having been cold compression-molded and then sintered.

2. The prosthetic teeth and bones of claim 1, wherein the amount of the weight proportion of $Ca_{10}(PO_4)_6(OH)_2$ to said additive is about 50 to 99.9% by weight of $Ca_{10}(PO_4)_6(OH)_2$ to about 0.1 to about 50% by weight.

3. The prosthetic teeth and bones of claim 1, wherein the fibrous material is arranged both lengthwise and crosswise.

4. The prosthetic teeth and bones of claim 3, wherein the fibrous material is in the form of a fabric.

5. The prosthetic teeth and bones of claim 4, wherein the fibrous material is in the form of a woven fabric.

6. The prosthetic teeth and bones of claim 4, wherein the fibrous material is in the form of a knitted fabric.

7. The prosthetic teeth and bones of claim 4, wherein the fibrous material is woven silicate glass fiber fabric.

8. The prosthetic teeth and bones of claim 1, wherein the sintering is performed at a temperature of about 800° to about 1500° C. for about 15 minutes to about 40 hours.

* * * * *